US008081796B2

(12) United States Patent
Derzhi et al.

(10) Patent No.: US 8,081,796 B2
(45) Date of Patent: Dec. 20, 2011

(54) METHOD FOR DETERMINING PROPERTIES OF FRACTURED ROCK FORMATIONS USING COMPUTER TOMOGRAPIC IMAGES THEREOF

(75) Inventors: Naum Derzhi, Sugar Land, TX (US); Jack Dvorkin, Redwood City, CA (US); Qian Fang, Houston, TX (US); Zbigniew Wojcik, Houston, TX (US)

(73) Assignee: Ingrain, Inc., Houston, TX (US)

( * ) Notice: Subject to any disclaimer, the term of this patent is extended or adjusted under 35 U.S.C. 154(b) by 632 days.

(21) Appl. No.: 12/276,432

(22) Filed: Nov. 24, 2008

(65) Prior Publication Data

US 2010/0128933 A1 May 27, 2010

(51) Int. Cl.
*G06K 9/00* (2006.01)
*G01N 23/04* (2006.01)
(52) U.S. Cl. ............................ 382/100; 382/154; 378/53
(58) Field of Classification Search .................. 382/100, 382/107, 106, 103, 108–109, 131, 154, 162, 382/165, 168, 170, 173, 181, 189–194, 199, 382/221, 224, 232, 254, 274, 276, 285–292, 382/294, 305, 312; 166/298; 175/249, 17; 702/16; 378/53; 324/303; 367/14
See application file for complete search history.

(56) References Cited

U.S. PATENT DOCUMENTS

| | | | | |
|---|---|---|---|---|
| 5,335,724 A | * | 8/1994 | Venditto et al. | 166/298 |
| 5,877,995 A | * | 3/1999 | Thompson et al. | 367/14 |
| 6,516,080 B1 | * | 2/2003 | Nur | 382/109 |
| 6,742,603 B2 | * | 6/2004 | Polizzotti et al. | 175/17 |
| 6,807,487 B2 | * | 10/2004 | Khan | 702/16 |
| 6,933,719 B2 | * | 8/2005 | Thomann et al. | 324/303 |
| 7,869,565 B2 | * | 1/2011 | Wood et al. | 378/53 |
| 2005/0256643 A1 | | 11/2005 | Boitnott | |

FOREIGN PATENT DOCUMENTS

WO 2005/108965 A1 11/2005
WO 2008070526 A2 6/2008

OTHER PUBLICATIONS

Knackstedt M A et al, "Digital Core Laboratory: Properties of reservoir core derived from 3D images," SPE Asia Pacific Conference on Integrated Modeling for Asset Management, No. 87009, Mar. 29, 2004, pp. 1-14.
Sakellariou et al, "Developing a virtual materials laboratory," Materials Today, Elsevier Science, Kidlington, GB, vol. 10, No. 12, Dec. 1, 2007, pp. 44-51.
Youssef N et al, "High Resolution CT and Pore-Network Models to Assess Petrophysical Properties of Homogeneous and Heterogeneous Carbonates," SPE/EAGE Reservoir Characterization and Simulation Conference, Abu Dhabi, No. 111427, Oct. 29, 2007, pp. 1-12.

(Continued)

*Primary Examiner* — Seyed Azarian
(74) *Attorney, Agent, or Firm* — Kilyk & Bowersox, P.L.L.C.

(57) ABSTRACT

A method for estimating a petrophysical parameter from a rock sample includes making a three dimensional tomographic image of the sample of the material. The image is segmented into pixels each representing pore space or rock grain. Porosity of the sample is determined from the segmented image. An image of at least one fracture is introduced into the segmented image to generate a fractured image. The porosity of the fractured image is determined. At least one petrophysical parameter related to the pore-space geometry is estimated from the fractured image.

12 Claims, 4 Drawing Sheets

OTHER PUBLICATIONS

Sarti A et al., "Detection and characterization of planar fractures using a 3D Hough transform," Signal Processing, Elsevier Science Publishers B.V. Amsterdam, NL, vol. 82, No. 9, Sep. 1, 2002, pp. 1269-1282.

Notification of transmittal of the international search report and the written opinion of the international searching authority, or the declaration, International application No. PCT/US2009/065429, Feb. 26, 2010.

Bugani et al, "Investigating morpholgical changes in treated vs. untreated stone building materials by x-ray micro-CT", Anal Boiannal. Chem (2008); 391.1343-1350.

Felipuissi et al, Measuring Statistical Geometric Properties of Tomographic Images of Soils, IEEE Trnasactions on Instrumentation and Measurement v. 57, No. 11.

E. Galluci et al., "3D experimental investogation of the microstructure of cement pastes . . . ", Cement and Concrete Research 37 (2007) 360-368.

De Graef et al, "A sensititvity study for the visualization of bacterial weathering of concrete and stone . . . " Science of the Total Environment 341 (2005) 173-183.

Jones et al., "Chracterization of methane hydrate host sediments using synchrotron-computer miccrtotomography,"J. Petr. Sci. and Eng. 56 (2007) 136-145.

Oren et al., Numerical Simulations of NMR Responses for Improved Interpretations of NMR Measurements in Reservoir Rocks, SPE paper 77398, Sep. 2002.

Arns et al., Computation of linear elastic properties from micrographic images: Methodology and agreement between theory and expreiment, Geophysics, vol. 67, No. 5, Sep.-Oct. 2002.

Fredrich et al., Predicting Macroscopic Transport Properties Using Microscopic Image Data, J. Geophysical Research, vol. 111, B03201, Mar. 2006.

Auzerais et al., Transport in Sandstone: A Study Based on Three Dimensional Microtomography, Geophysical Research Letters, vol. 23, No. 7, Apr. 1996.

Arns, et al., Digital Core Laboratory: Petrophysical Analysis from 3D Imaging of Core Fragments, Petrophysics, vol. 46, No. 4, Aug. 2005.

Saenger et al, Finite Difference Modeling of Wave Propagation on Microscale: A Snapshot of the Work in Progress, Geophysics vol. 72, No. 5, Sep.-Oct. 2005.

\* cited by examiner

METHOD FOR DETERMINING PROPERTIES OF FRACTURED ROCK FORMATIONS USING COMPUTER TOMOGRAPIC IMAGES THEREOF

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The invention relates generally to the field of estimating material properties of porous media. More specifically, the invention relates to methods for estimating such properties using computer tomographic (CT) images of porous media such as subsurface rock formation.

2. Background Art

Estimating material properties such as effective elastic moduli, electrical resistivity and fluid transport properties of porous media, for example, mobility of hydrocarbon in subsurface rock formations, has substantial economic significance. Methods known in the art for identifying the existence of subsurface hydrocarbon reservoirs, including seismic surveying and well log analysis, need to be supplemented with reliable methods for estimating how fluids disposed in the pore spaces of the reservoir rock formations will flow over time in order to characterize the economic value of such reservoir rock formations.

One method known in the art for estimating fluid transport properties is described in U.S. Pat. No. 6,516,080 issued to Nur. The method described in the Nur patent includes preparing a "thin section" from a specimen of rock formation. The preparation typically includes filling the pore spaces with a dyed epoxy resin. A color micrograph of the section is digitized and converted to an n-ary index image, for example a binary index image. Statistical functions are derived from the two-dimensional image and such functions are used to generate three-dimensional representations of the rock formation. Boundaries can be unconditional or conditioned to the two-dimensional n-ary index image. Desired physical property values are estimated by performing numerical simulations on the three-dimensional representations. For example, permeability is estimated by using a Lattice-Boltzmann flow simulation. Typically, multiple, equiprobable three-dimensional representations are generated for each n-ary index image, and the multiple estimated physical property values are averaged to provide a result.

In performing the method described in the Nur patent, it is necessary to obtain samples of the rock formation and to prepare, as explained above, a section to digitize as a color image. Economic considerations make it desirable to obtain input to fluid transport analysis more quickly than can be obtained using prepared sections. Recently, devices for generating CT images of samples such as drill cuttings have become available. Such CT image generating devices (CT scanners) typically produce three-dimensional gray scale images of the samples analyzed in the scanner. Such gray scale images can be used essentially contemporaneously as drill cuttings are generated during the drilling of a wellbore through subsurface rock formations.

Using images of samples of rock formations it is possible to obtain estimates of petrophysical parameters of the imaged rock sample, for example, porosity, permeability, shear and bulk moduli, and formation resistivity factor.

The transport properties of certain rock types, e.g., diatomites, shales, tight gas sandstone, tight carbonates, and chalks, are substantially affected by thin fractures (or cracks) that connect otherwise disconnected pore space. The spacing between these fractures may be large and, as a result, these fractures may not be captured in selected rock fragments subject to imaging using conventional imaging techniques, including CT scan images. Petrophysical properties of such formations may be incorrectly determined or estimated if the estimates are based on such images.

There exists a need to use images such as the foregoing CT scan images to estimate petrophysical properties of fractured rock formations.

SUMMARY OF THE INVENTION

A method for estimating a petrophysical parameter from a rock sample according to one aspect of the invention includes making a three dimensional tomographic image of the sample of the material. The image is segmented into pixels each representing pore space or rock grain. Porosity of the sample is determined from the segmented image. An image of at least one fracture is introduced into the segmented image to generate a fractured image. The porosity of the fractured image is determined. At least one petrophysical parameter related to the pore space geometry thus altered is estimated from this fractured image.

Other aspects and advantages of the invention will be apparent from the following description and the appended claims.

DETAILED DESCRIPTION

Figure 1:
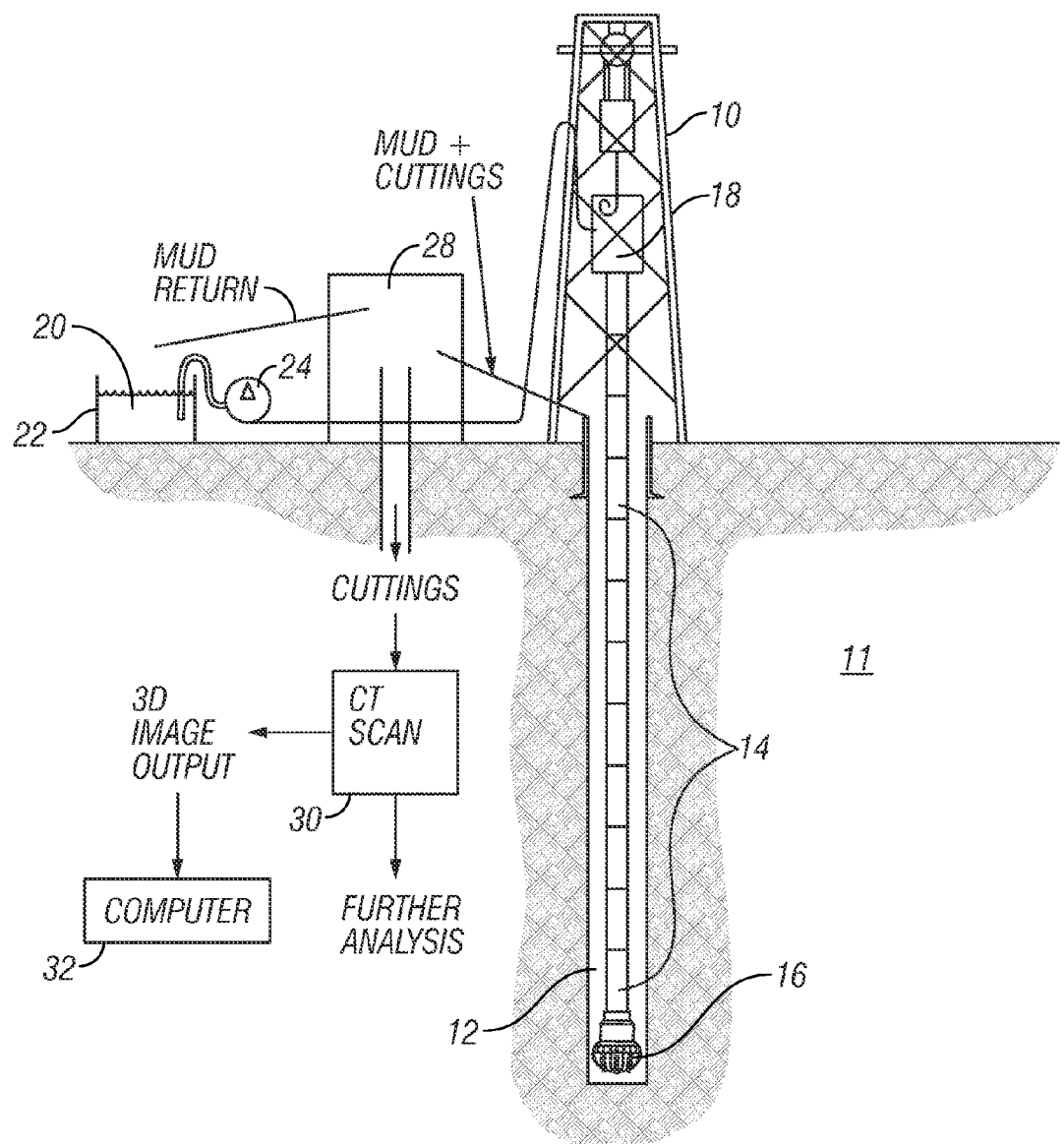
FIG. 1 shows an example of obtaining cuttings during drilling of a wellbore and analysis thereof during the drilling.

The description of this invention is made with reference to using drill cuttings obtained during the drilling of a wellbore through subsurface formations. It should be clearly understood that drill cuttings is only one example of samples of rock formation that may be used with the present invention. Any other source of a rock formation sample, e.g., whole cores, sidewall cores, outcrop quarrying, etc. may provide suitable samples for analysis using methods according to the invention. Consequently, the invention is not limited in scope to analysis of drill cuttings.

An example of drilling a wellbore to obtain samples of rock formations for evaluation by examples of a method according to the invention will be explained with reference to FIG. 1. A drilling unit or "rig" 10 is disposed at the Earth's surface. The rig 10 includes lifting equipment (not shown separately) for raising and lowering one of several types of device used to rotate a drill string 14. The device, shown at 18 in the present example may be a top drive, although the use of a top drive is not a limit on the scope of the invention. The drill string 14 is assembled by threadedly coupling segments of drill pipe end to end. A drill bit 16 is disposed at the lower end of the drill string 14 and cuts through subsurface rock formations 11 to form a wellbore 12. During the drilling of the wellbore 12, the rig 10 is operated to cause some of the axial load (weight) of the drill string 14 to be applied to the drill bit 16. The top drive 18 rotates the drill string 14 and the drill bit 16 at the lower end thereof. The combination of axial load and rotation causes the drill bit 16 to cut through the formations 11.

The rig 10 includes a tank or pit 22 having drilling fluid ("mud") 20 stored therein. A pump 24 lifts the mud 20 and discharges it through suitable flow lines 26 so that the mud 20 passes through an internal passage in the drill string 14, whereupon it is discharged through suitable orifices or courses in the drill bit 16. The discharged mud 20 cools and lubricates the drill bit 16 and lifts the cuttings generated by the bit 16 to the Earth's surface. The cuttings and mud thus lifted enter separation and cleaning devices, shown generally at 28 and including, for example, devices known as "degassers" and "shale shakers" to remove the cuttings and contamination from the mud 20. The mud after such cleaning is returned to the pit 22 for subsequent use in drilling the wellbore 12.

In the present example, the cuttings removed from the separation and cleaning device 28 may be transported to a computer tomographic ("CT") scanner 30, which may use x-rays for analysis of internal structure of the cuttings, for generation of three dimensional (3D) images of the cuttings. The images so generated may be in numerical form and their content will be further explained below. After CT scanning, the cuttings may be saved for further analysis or may be suitably discarded. An example of a suitable CT scanner for making images usable with methods according to the invention is sold under model designation MicroXCT Series 3D tomographic x-ray transmission microscope by Xradia, Inc., 5052 Commercial Circle, Concord, Calif. 94520.

In some examples, an analysis of the cuttings from the CT scan images may provide, substantially in real time during the drilling of the wellbore, an estimate of certain properties of the subsurface formations being drilled, for example fluid mobility of one or more constituent fluids in the pore spaces of the rock formations 11. In the present example, images generated by the CT scanner 30 may be transferred to a computer 32 having program instructions for carrying out image analysis and subsequent formation property modeling as described below.

It should also be understood that drill cuttings are only one type of rock sample that may be analyzed according to the invention. In other examples, the drill but 16 may be an annular type configured to drill whole cores of the rock formations 11. In other examples, percussion sidewall core samples may be obtained during drilling or when the drill string 14 is withdrawn from the wellbore 12 such as for "wireline" well evaluation techniques. Also as explained above, rock samples may be obtained from sources other than a wellbore. Accordingly, the scope of the invention is not limited to analysis of drill cuttings or other samples obtained from a wellbore.

CT scan imaging of a porous material sample (e.g., a sample of rock formation) is used in the method to produce a numerical object that represents the material sample digitally in the computer 32 for subsequent numerical simulations of various physical processes, such as viscous fluid flow (for permeability estimation); stress loading (for the effective elastic moduli); electrical current flow (for resistivity); and pore size distribution for nuclear magnetic resonance relaxation time properties, including distribution of relaxation time. In some examples, such analysis can be performed while drilling operations are underway, substantially in real time.

The CT scan image produced by the CT scanner 30 may be a 3D numerical object consisting of a plurality of 2D sections of the imaged sample. Each 2D section consists of a grid of values each corresponding to a small region of space defined within the plane of the grid. Each such small region of space is referred to as a "pixel" and has assigned thereto a number representing the image darkness (or for example the density of the material) determined by the CT scan procedure. The value ascribed to each pixel of the 2D sections is typically an integer that may vary between zero and 255 where 0 is, e.g., pure white, and 255 is pure black. Such integer is typically referred to as a "gray scale" value. 0 to 255 is associated with eight digital bits in a digital word representing the gray scale value in each pixel. Other gray scale ranges may be associated with longer or shorter digital words in other implementations, and the range of 0 to 255 is not intended to limit the scope of the invention. For the purpose of simulating a physical process using such a numerical object (the gray scale), however, the numerical object is preferably processed so that all the pixels allocated to the void space in the rock formation (pore space) are represented by a common numerical value, e.g., by only 255s, and all the pixels associated with the rock matrix (or rock grains) are represented by a different numerical value, for example, zeroes. The foregoing process is called image segmentation. Subsequently, the resulting numerical object can be normalized so that the pore spaces are represented by, for example, ones and the rock grains are represented by zeroes. The foregoing may be described as converting the image into a binary index. In other examples, the image may be converted into an index having any selected number, n, of indices. It has been determined that sufficiently accurate modeling of rock properties may be obtained using a binary index, in which one value represents pore space and another single value represents rock grains.

A technique known in the art for segmenting a gray-scale object is called "thresholding", where all pixels having a gray scale value below a selected threshold value (e.g., a gray scale value of 150 on a scale of 0 to 255) are identified as grains, while all other pixels are identified as pore space. The foregoing approach is often not satisfactory, however, because, due to numerical clutter in an unprocessed CT scan image, some pixels physically located inside a grain may have the gray level of the pore space and vice versa. In the invention, a type of image segmentation known as "region growing" can be used. Region growing may be described as follows. Consider a 2D section of a CT scan image made of a porous rock formation such as sandstone, which has primarily quartz rock grains. A substantial number of "seeds" (each seed consists of one or more pixels having a similar pixel gray scale level, e.g., 250±5) is placed within the image. All pixels within a seed are assigned the same gray scale level which may be an average (e.g., arithmetic) of the gray levels of all the pixels within the seed. The seeds in the image frame do not overlap spatially. Next, two or more adjacent seeds are merged and are identified as a "region" if the gray scale levels of the adjacent seeds have gray scale values within a selected difference threshold of each other. Each identified region is assigned a uniform (fixed) gray level, which can be a weighted average of the gray scale values of all the seeds that have been merged into the identified region. The foregoing process continues for all regions thus formed in the image frame. As a result, the unprocessed CT image is transformed into internally uniform regions plus unclassified pixels that were not assigned to any of the identified regions (because such pixels included gray scale values outside the allocation threshold criteria). Each of such unclassified pixels can be assigned to an adjacent region with the closest gray scale level. If the resulting number of regions is greater than two, however, the foregoing method simply fails to allocate the CT image correctly into grains and pores.

To address the foregoing problem with extending ("growing") seeds into regions, in the invention, instead of using seeds having different gray scale values, only two classes of seeds are used: all pixels having a gray scale value below a selected initial limit for the gray scale level of rock grains (e.g., 60) are classified as rock grains; and all pixels in which the gray scale level is larger than a selected initial limit for pore spaces (e.g., 130) are classified as pore space. One simple way of specifying these initial limits is by selecting the gray scale levels corresponding to the peaks of a gray level histogram. In many subsurface formations, such a histogram will be bimodal, wherein one mode value will correspond to the gray scale level of pores, and another mode value will correspond to the gray scale level of rock grains.

The next element in image classification according to the invention is to grow each of the two initially formed seeds by allocating to such seeds all adjacent pixels having gray scale levels within a selected tolerance, e.g., 130−5 for pore spaces and 60+5 for rock grains. The foregoing process can continue by incrementally increasing the gray scale lower limit for rock grains and incrementally reducing the gray scale upper limit for pore spaces until the two limits meet. The result is that all pixels will be allocated to either pore space or to rock grains, thus providing a fully segmented image.

A possible advantage of the foregoing procedure is that instead of forming multiple regions, the foregoing technique grows only two distinctive regions from start to end, thus avoiding the situation where multiple distinctive regions appear and then have to be reclassified into either pores or grains. If the resulting segmented image appears noisy (cluttered), it can be smoothed by any of conventional filters.

A schematic outline of the foregoing procedure follows. First is to preprocess the original image using the median or 2D Gaussian kernel filter. The size of the filter is provided by the user and should depend on, among other factors, the quality of the image (level of noise). It should be noted that the image segmenting procedure that follows has been demonstrated to be sufficiently noise resistant as to make the pre-processing frequently unnecessary.

Next, two user-selected thresholds, $t_1$ and $t_2$, are selected to determine initial regions for pore space and rock grains, respectively. The initial thresholds may be selected, for example, by analysis of a histogram of the gray scale values in the CT image. For every pixel $p_i$ having a gray scale level represented by $B(p_i)$:

if $B(p_i) > t_1$ then $p_i$ is identified as pore space; and
if $B(p_i) < t_2$ then $p_i$ is identified as rock grain.

If there are two or more contiguous pixels in any subset of the image frame that are classified according to the threshold procedure above, such contiguous pixels may be referred to as "clusters." All of the pixels allocated as explained above then become the image seeds from which region growing proceeds.

Finally, for each pixel classified as a pore, its eight neighbors (spatially contiguous pixels) in the 2D image plane are interrogated. If any of the interrogated neighbor pixels is not already identified as pore or rock grain, and the gray scale level of such pixel is within a preselected tolerance level of (or initially selected different between) the gray scale level assigned to the "pore" seed (as in Step 2 above), the interrogated neighbor pixel is then classified as a pore and is allocated to the "pore" cluster.

The foregoing contiguous pixel interrogation is also performed for pixels classified as rock grain. Contiguous, previously unallocated pixels having gray scale level within a preselected tolerance of the gray scale level of the rock grain seed are allocated to the rock grain cluster.

The foregoing cluster allocation and region growing process continues for both pore space and rock grain until all the pixels in the 2D image frame are interrogated. If any of the pixels is not classified as pore space or rock grain, the foregoing tolerance value for each of the pore space and the rock grain may be increased by a selected increment (for example five gray scale numbers), and the contiguous pixel interrogation and classification may be repeated. The foregoing tolerance increase and repeated adjacent pixel interrogation may be repeated until all or substantially all the pixels in the 2D image frame are allocated to either rock grain or pore space.

The foregoing region growing procedure is then repeated for each 2D image frame in the 3D CT scan image. The result is a three dimensional characterization of the pore structure of the rock samples on which CT imaging has been performed.

Figure 2:
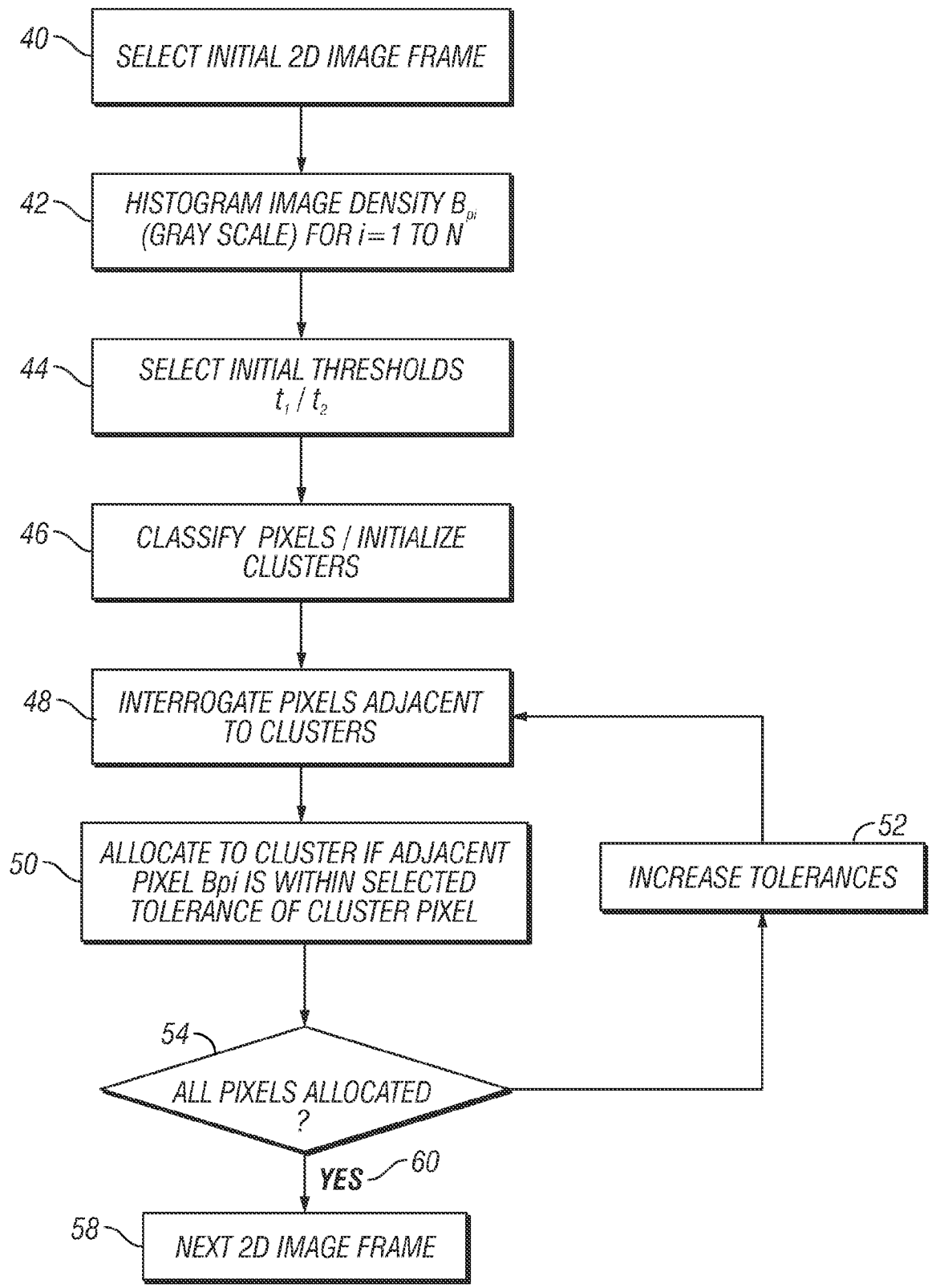
FIG. 2 shows a flow chart of an example process for CT image segmentation.
Figure 3A:
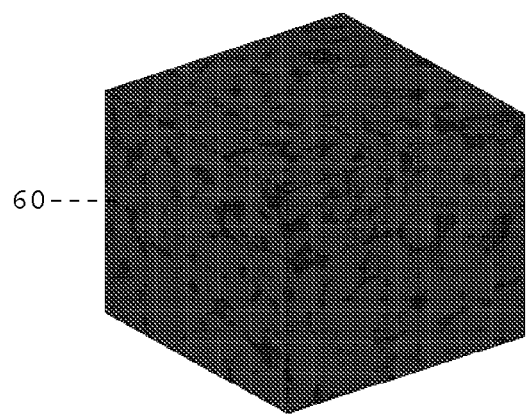
FIGS. 3A through 3D show, respectively, examples of unfractured rock samples, and introduction of three different fractures in the rock sample of FIG. 4A.
Figure 3B:
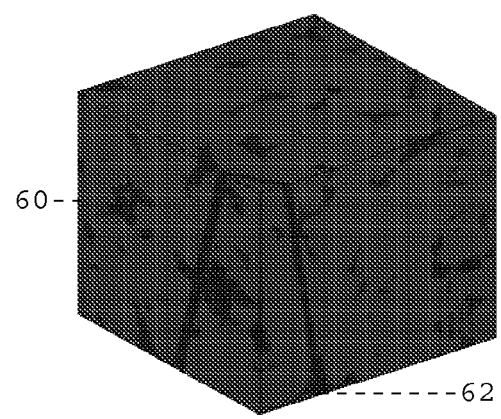
Figure 3C:
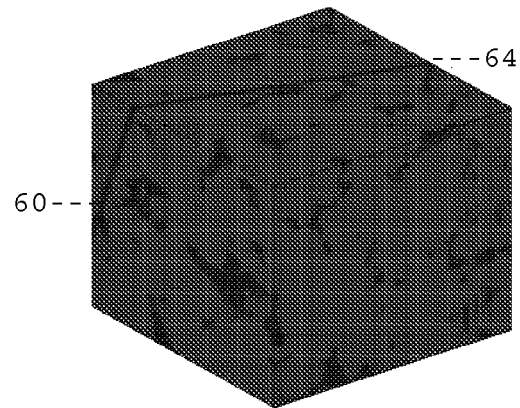
Figure 3D:
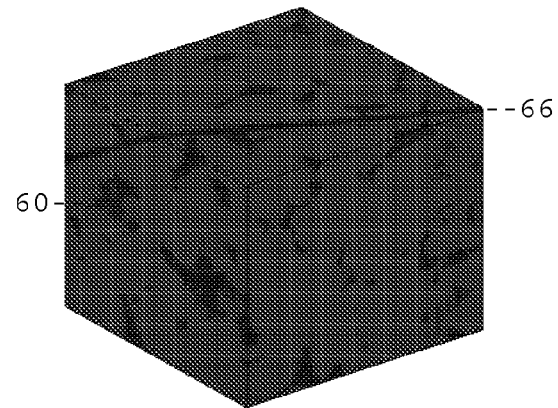

An example implementation of the above process for image segmentation is shown in a flow chart in FIG. 2. At 40, a 2D image frame of a CT scan image is selected. The image frame may be subjected to histogram analysis, at 42 to determine possible mode values of gray scale for pore spaces and for rock grains. At 44, the possible modes of the histogram may be used to set initial values for the image segmentation thresholds $t_1$ and $t_2$. At 46, using the initial segmentation thresholds, all pixels in the image frame are interrogated may be are allocated to pore space or to rock grains, depending on whether the gray scale value in each pixel exceeds the respective segmentation threshold. The allocated pixels are then segmented into seeds where two or more contiguous pixels are allocated to either pore space or rock grain. At 48, pixels adjacent to the each of the seeds are interrogated. Previously unallocated pixels having a gray scale value falling within an initially selected threshold difference (or tolerance) of the adjacent cluster pixel gray scale value are allocated to the seed at 50. At 54, the image frame is interrogated to determine if all or substantially all the image frame pixels have been allocated to either pore space or rock grain. At 54, the number of allocated pixels is counted and at 60 if all or substantially all the pixels in the image frame have been allocated, a new 2D image frame can be selected, at 58, and the above process repeated. Typically the next 2D image frame will be adjacent to the most recently analyzed 2D image frame. The above process can be repeated until all available 2D image frames have been analyzed. If all pixels in the image frame have not been allocated, at 52, the tolerance or difference threshold values used at 50 may be increased and the interrogation of pixels adjacent to the existing seeds can be repeated, at 48, and the remainder of the process can be repeated.

The result of the foregoing procedure is a segmented 3D image of the rock sample including image elements for rock grain and for pore space. Such image can be stored or displayed in a computer and can be used as input to one or more rock property characterization models as will be further explained below.

In a method according to the invention, images of "fractures" are introduced into the rock sample image obtained and segmented as explained above. The preferred orientation of the fractures and their aperture (thickness) may be obtained, for example, from well microimages such as may be obtained from well logging instruments, outcrop studies, and/or any geological and petrophysical information that is available. The "fractured" image can then be used to calculate one or more petrophysical properties (e.g., permeability) of the fractured formation. The "fracture" may be introduced into the image by defining a fracture plane with reference to the image volume and then changing the value of each image pixel at a selected distance normal to the fracture plane from rock grain to pore space. The selected distance normal to the plane (in pixels) defines the fracture aperture or thickness. The plane and thickness define a fracture volume. Pixels determined to be within the defined fracture volume that are already designated as pore space in the segmented image may remain designated as pore space after introduction of the fracture to the image.

Examples of introducing fractures in a segmented rock sample image are shown in FIGS. 3A through 3D. The original, segmented image of the formation sample is shown at 60. One fracture having a selected orientation is shown at 62 in FIG. 3B. Corresponding fractures having different orientations are shown, respectively, at 64 and 66 in FIGS. 3C and 3D. The resulting formation porosity (determined by pore and rock grain pixel count) changes and also resulting permeability (determined using fluid transport modeling as explained below) changes are tabulated in Table 1.

TABLE 1

Porosity and permeability for the samples shown in FIG. 1.
The permeability is shown in the x, y, and z directions.

| Sample | Porosity | Permeability X | Permeability Y | Permeability Z |
|---|---|---|---|---|
| Unfractured | 0.138 | 59 | 61 | 66 |
| Fracture A | 0.147 | 63 | 76 | 333 |
| Fracture B | 0.163 | 171 | 517 | 537 |
| Fracture C | 0.159 | 427 | 614 | 69 |

Calculating the plane for purposes of introducing it into the image may be understood mathematically as follows. The equation for a plane passing through a point $(x_0,y_0,z_0)$ and normal to a vector $\vec{n}=(a,b,c)$ is given by the expression.

$$ax+by+cz+d=0,$$

where $d=-ax_0-by_0-cz_0$ and $(x,y,z)$ is a rectangular coordinate system

The distance D from a point $(x_1,y_1,z_1)$ to the foregoing plane is given by the expression:

$$D = \left| \frac{ax_1 + by_1 + cz_1 + d}{\sqrt{a^2 + b^2 + c^2}} \right|.$$

Thus, using the above expressions, it is possible to define a set of pixels to be changed from rock grain to pore space to provide the equivalent of a fracture in the segmented image of the rock sample.

Figure 4:
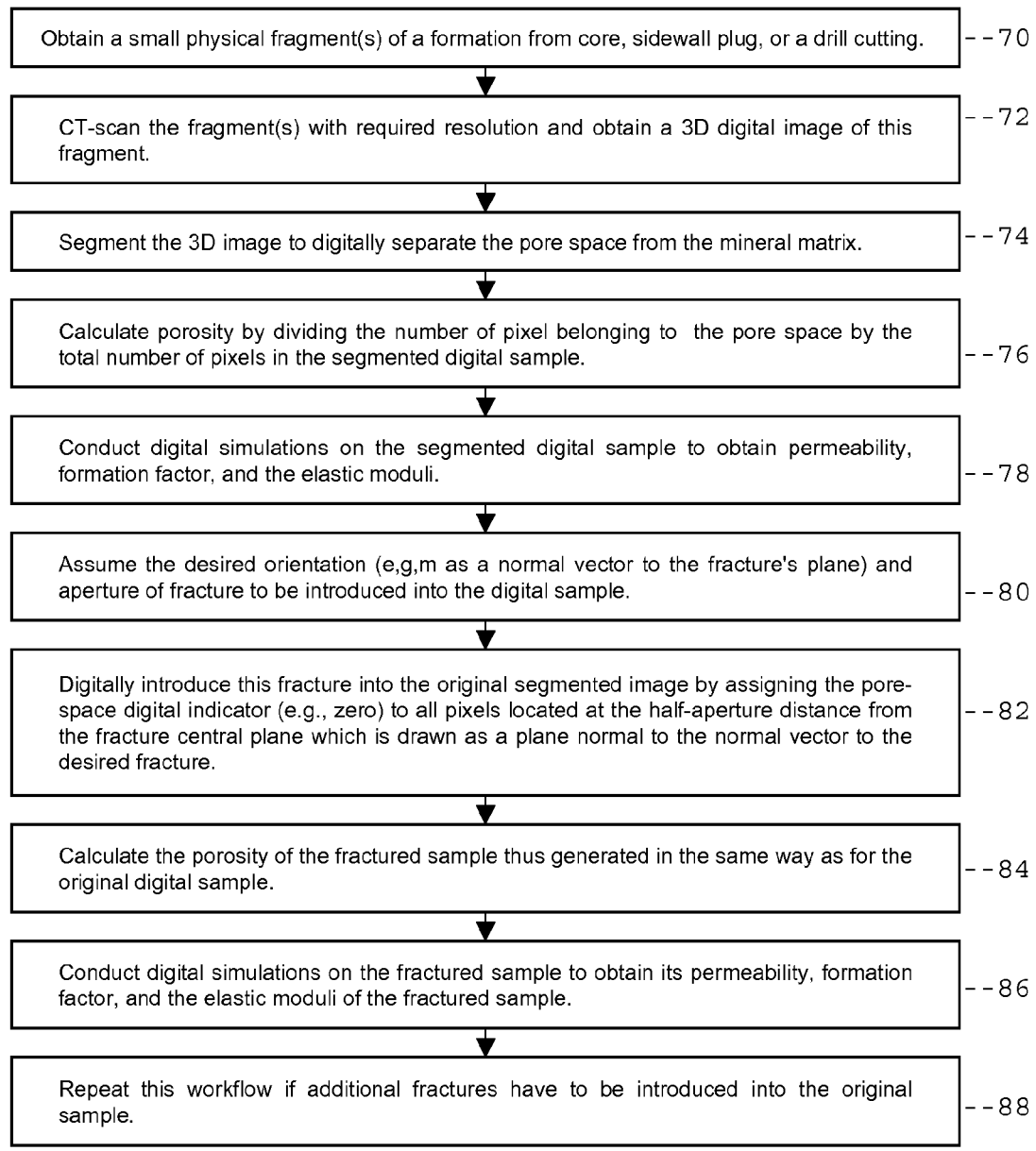
FIG. 4 shows a flow chart of one example of a method according to the invention.

A flow chart showing an example of a method according to the invention will be explained with reference to FIG. 4. At 70, a sample of a rock formation is obtained, such as from drill cuttings (FIG. 1), whole core samples obtained by drilling, outcrop samples or any other source of rock formation sample. At 72, the rock sample is CT imaged (FIG. 1). The image obtained may then be segmented, at 74. In one example, the image is segmented using the technique explained above with reference to FIG. 2.

At 76, porosity of the rock sample is obtained from the segmented image. The porosity may be obtained, for example, by counting pixels allocated to each of pore space and rock grain. Using the porosity determined as explained above, at 78, one or more petrophysical parameters may be estimated. Techniques for such estimation are known in the art, and several examples are described below.

At 80, a direction of a fracture is determined, using information such as described above. At 82, the fracture is introduced into the image by changing pixel values along the plane from rock grain to pore space. At 84, the porosity of the "fractured" formation image is determined. At 86, one or more petrophysical parameters, including, for example, permeability, formation resistivity factor and elastic and shear moduli may be estimated using the fractured image porosity. Example techniques for estimating such parameters are described below. At 88, additional or different fractures may be introduced into the image and the process may be repeated starting at 82.

In the present example, the Lattice-Boltzmann method can be used to numerically solve Navier-Stokes equations for flow simulation for permeability modeling. Such solution may be used to calculate permeability of simulated 3D volumes. The Lattice-Boltzmann method is a robust tool for flow simulation, particularly in media with complex pore geometry. See, for example. Ladd, *Numerical Simulations of Particulate Suspensions via a discretized Boltzmann Equation, Part 1: Theoretical Foundation*, J. Fluid Mech., v 271, 1994, pp. 285-309; Gunstensen et al., "*Lattice Boltzmann Model of Immiscible Fluids*, Phys. Rev. A., v. 43, no. 8, Apr. 15, 1991, pp. 4320-4327; Olsen et al., *Two-fluid Flow in Sedimentary Rock: Simulation, Transport and Complexity*, J. Fluid Mechanics, Vol. 341, 1997, pp. 343-370; and Gustensen et al., *Lattice-Boltzmann Studies of Immiscible Two-Phase Flow Through Porous Media*," J. of Geophysical Research, V. 98, No. B 4, Apr. 10, 1993, pp. 6431-6441).

The Lattice-Boltzmann method simulates fluid motion as collisions of imaginary particles, which are much larger than actual fluid molecules, but wherein such particles show almost the same behavior at a macroscopic scale. The algorithm used in the Lattice-Boltzmann method repeats collisions of these imaginary particles until steady state is reached, and provides a distribution of local mass flux. In accordance with the present invention, the Lattice-Boltzmann method is applied successfully for many pore structures, including cylindrical tubes, random densely packed spheres, and 3D rock samples digitized by CT scanning as explained above. See, for example, U.S. Pat. No. 6,516,080 issued to Nur.

It is also possible to estimate capillary pressure related flow characteristics from the pore structure determined using the 3D images processed as explained above. See, for example, U.S. Pat. No. 7,277,795 issued to Boitnott. Any or all of the foregoing estimated physical properties may be stored and/or displayed in the computer (32 in FIG. 1).

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for estimating a petrophysical parameter of a porous material from a sample thereof, comprising:
   making a three dimensional tomographic image of the sample of the material;
   segmenting the image into pixels each representing pore space or rock grain;
   determining porosity of the sample from the segmented image;

introducing an image of at least one fracture into the segmented image to generate a fractured image;

determining porosity of the fractured image;

determining at least one petrophysical parameter comprising permeability, electrical resistivity formation factor, elastic modulus, bulk modulus or shear modulus; and at least one of storing and displaying the at least one petrophysical parameter.

2. The method of claim 1 wherein the tomographic image comprises a value of gray scale allocated to each of a plurality of pixels in the image.

3. The method of claim 2 wherein the segmenting comprises:

(a) determining an initial gray scale threshold for each of pore space and rock grain;

(b) allocating each pixel in the image to pore space or rock grain for each pixel meeting threshold criteria for each of the pore space and rock grain thresholds, respectively;

(c) interrogating pixels adjacent to each seed;

(d) allocating the interrogated adjacent pixels previously not allocated to a seed to the pore space seed or the rock grain seed based on threshold criteria; and (e) repeating (c) and (d) until substantially all pixels in the image are allocated to the rock grain or the pore space.

4. The method of claim 3 wherein the determining initial gray scale thresholds comprises histogram analysis of the tomographic image.

5. The method of claim 3 wherein the allocating interrogated adjacent pixels comprises determining a difference between a gray scale value and a gray scale value of the adjacent pixel in the seed, and allocating the interrogated pixel to the seed if the difference falls below a selected threshold.

6. The method of claim 5 further comprising:

determining whether unallocated pixels exist in the image;

increasing the selected difference threshold; and repeating the interrogating adjacent and allocating the interrogate pixels having gray scale values wherein the difference is below the increased difference threshold.

7. The method of claim 1 wherein the material comprises a rock formation.

8. The method of claim 7 wherein the at least one petrophysical parameter comprises permeability.

9. The method of claim 8 wherein permeability is estimated using the Lattice-Boltzmann approximation.

10. The method of claim 7 wherein the at least one petrophysical parameter comprises electrical resistivity formation factor.

11. The method of claim 7 wherein the at least one petrophysical parameter comprises at least one of elastic modulus, bulk modulus and shear modulus.

12. The method of claim 1 wherein the introducing at least one fracture includes defining a plane at a selected orientation with respect to the segmented image, and changing pixels allocated to rock grain into pixels allocated to pore space at a selected distance normal to the defined plane.

* * * * *

UNITED STATES PATENT AND TRADEMARK OFFICE
CERTIFICATE OF CORRECTION

PATENT NO. : 8,081,796 B2
APPLICATION NO. : 12/276432
DATED : December 20, 2011
INVENTOR(S) : Derzhi et al.

It is certified that error appears in the above-identified patent and that said Letters Patent is hereby corrected as shown below:

Title page item [54]

Line 3, "TOMOGRAPIC" should read --TOMOGRAPHIC--.

Signed and Sealed this
First Day of May, 2012

David J. Kappos
*Director of the United States Patent and Trademark Office*

UNITED STATES PATENT AND TRADEMARK OFFICE
CERTIFICATE OF CORRECTION

PATENT NO. : 8,081,796 B2  
APPLICATION NO. : 12/276432  
DATED : December 20, 2011  
INVENTOR(S) : Derzhi et al.

Page 1 of 1

It is certified that error appears in the above-identified patent and that said Letters Patent is hereby corrected as shown below:

Title page item [54] and at Column 1, line 3, in the title,

"TOMOGRAPIC" should read --TOMOGRAPHIC--.

This certificate supersedes the Certificate of Correction issued May 1, 2012.

Signed and Sealed this  
Twenty-ninth Day of May, 2012

David J. Kappos  
*Director of the United States Patent and Trademark Office*